(12) United States Patent
Jelic et al.

(10) Patent No.: US 11,478,276 B2
(45) Date of Patent: Oct. 25, 2022

(54) EXTERNAL LOAD BEARING DISTRACTING DEVICE FOR AN ARTICULATING ANATOMICAL JOINT

(71) Applicant: Flexi Oscar d.o.o., Zagreb (HR)

(72) Inventors: Mislav Jelic, Zagreb (HR); Slobodan Vukicevic, Zagreb (HR)

(73) Assignee: Flexi Oscar d.o.o.

( * ) Notice: Subject to any disclaimer, the term of this patent is extended or adjusted under 35 U.S.C. 154(b) by 223 days.

(21) Appl. No.: 16/627,909

(22) PCT Filed: May 14, 2018

(86) PCT No.: PCT/EP2018/025138
§ 371 (c)(1),
(2) Date: Dec. 31, 2019

(87) PCT Pub. No.: WO2019/007550
PCT Pub. Date: Jan. 10, 2019

(65) Prior Publication Data
US 2021/0137562 A1 May 13, 2021

(30) Foreign Application Priority Data

Jul. 3, 2017 (GB) ..................................... 1710591

(51) Int. Cl.
*A61B 17/64* (2006.01)
*A61B 17/66* (2006.01)
(Continued)

(52) U.S. Cl.
CPC .......... *A61B 17/6425* (2013.01); *A61B 17/66* (2013.01); *A61B 17/846* (2013.01); *A61B 2017/567* (2013.01)

(58) Field of Classification Search
CPC ... A61B 17/6425; A61B 17/66; A61B 17/846; A61B 2017/567
(Continued)

(56) References Cited

U.S. PATENT DOCUMENTS 5,941,877 A * 8/1999 Viegas ............... A61B 17/6425
606/55
6,056,748 A * 5/2000 Weiner ............... A61B 17/6425
606/54
(Continued)

FOREIGN PATENT DOCUMENTS

| DE | 102006027155 A1 | 12/2007 |
|---|---|---|
| GB | 2519981 A | 5/2015 |
| WO | 2011049796 A2 | 4/2011 |

*Primary Examiner* — Eduardo C Robert
*Assistant Examiner* — David C Comstock
(74) *Attorney, Agent, or Firm* — St Onge Steward Johnston and Reens LLC (57) ABSTRACT

An external load bearing distracting device, which can be positioned to fully unload a knee joint cartilage while providing the knee joint normal motion, for an articulating anatomical joint. The device includes first and second rotatable extensions arranged longitudinally on opposite sides of the joint, and first and second translational inserts slidably arranged inside the first and second rotatable extensions, respectively. The joint may comprise a ball-and-ring-joint or a cardan joint. The first and second translational inserts include a threaded portion and a pair of threaded nuts thereon, which abut a retainer on each of the first and second rotatable extensions to limit longitudinal translation. The external load-bearing distracting device is temporarily attached to the patient, preferably for a period of 6 to 8 weeks, and is intended for use to treat osteoarthritis, focal cartilage defects, and fractures inside the knee joint, among other conditions of articulating anatomical joints.

31 Claims, 9 Drawing Sheets

(51) Int. Cl.
*A61B 17/84* (2006.01)
*A61B 17/56* (2006.01)

(58) Field of Classification Search
USPC .......................... 606/55, 57, 58, 59, 90, 105
See application file for complete search history.

(56) References Cited

U.S. PATENT DOCUMENTS

| | | | |
|---|---|---|---|
| 6,171,309 B1* | 1/2001 | Huebner | A61B 17/66 606/57 |
| 9,066,756 B2* | 6/2015 | Wong | A61B 17/6416 |
| 2004/0181221 A1* | 9/2004 | Huebner | A61B 17/6425 606/59 |
| 2004/0260302 A1 | 12/2004 | Manspeizer | |
| 2005/0015087 A1* | 1/2005 | Walulik | A61B 17/66 606/54 |
| 2006/0229605 A1* | 10/2006 | Olsen | A61B 17/66 606/54 |
| 2012/0143189 A1 | 6/2012 | Wolfson | |
| 2016/0022315 A1* | 1/2016 | Soffiatti | A61B 17/60 606/54 |

* cited by examiner

EXTERNAL LOAD BEARING DISTRACTING DEVICE FOR AN ARTICULATING ANATOMICAL JOINT

BACKGROUND OF THE INVENTION

Field of the Invention

The present invention relates to an external load bearing distracting device for an articulating anatomical joint. In a preferred embodiment, the articulating anatomical joint is a knee joint. More particularly, the present invention relates to the external load bearing distracting device which can be positioned to unload a knee joint while providing its normal motion and can be adjusted to distract and fully unload the knee joint cartilage. The present invention is intended for use particularly, but not exclusively, to treat osteoarthritis (OA), focal cartilage defects and treatment of fractures occurred inside the knee joint.

Brief Description of the Prior Art

The knee joint is subject to many types of traumatic injuries and pathological conditions which result in soft tissue rupture, dislocation, bone fracture, cartilage erosion, or infection. The current methods of treatment are usually rest, bracing, casting, internal fixation, external fixation, ligamentous reconstruction, prosthetic replacement or a combination of the above.

Immobilization has been found to be less than satisfactory because it can reduce subsequent motion of the joint, sometimes permanently. Soft tissue repairs are adversely affected by both immobilization and mobilization, unless the latter is prevented from overstretching the tissues before healing occurs.

External linkages would not suffer from the above shortcomings but have been unsatisfactory in the past because they provide only approximate motion and are not compatible with the more exacting motion requirements of the internal structures of the knee joint. A device which allows physiological motions of the knee and which in parallel provides unloading of the knee joint would thus be of a great clinical benefit and would enable further advances in the knee joint treatment.

It has been known that the joint surfaces of the knee undergo a combination of rolling and sliding, that the medial and lateral sides move differently and that there is a transverse rotation of the femur about the longitudinal axis of the tibia, especially towards the extension position. This is known as the "screw-home" mechanism. Actually, the movements of the knee joint include six degrees of freedom of motion namely 3 translations (antero-posterior, medio-lateral and distraction-compression) and 3 rotations (flexion-extension, varus-valgus and internal-external).

The physiological motion of the human knee involves an extremely complex "polycentric" motion wherein the center of rotation of the tibia with respect to the femur varies as a function of the angle of rotation. This motion is caused by simultaneous movements of the interacting surfaces involved in articulation of the knee, including: internal-external rotation of the tibia relative to the femur about a vertical axis; movement between the femoral and tibial parts about a horizontal, anterior-posterior axis; and sliding and anterior-posterior rolling of ends of the femoral and tibial parts in an anterior-posterior plane. The physiological motion of the tibia relative to the femur is further complicated by the three-dimensional component of motion outside the sagittal plane, and by the contribution of ligaments, tendons and cartilage structure.

Figure 1:
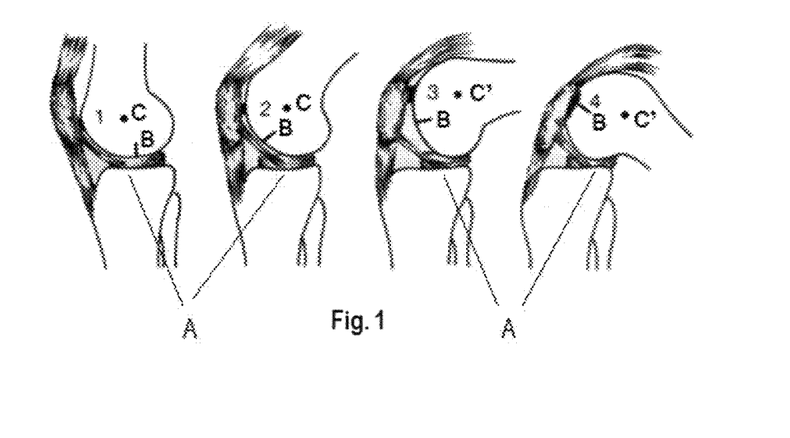
FIG. 1 is a schematic illustration, from the lateral or medial side, of a knee joint.
Figure 2:
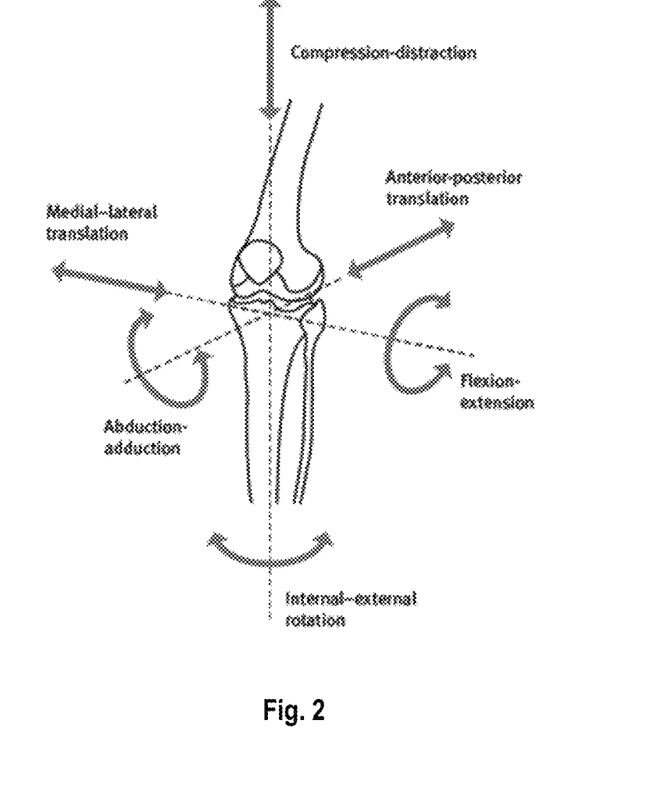
FIG. 2 is a schematic illustration of a knee joint degrees of freedom of movement.

The above can be best understood with reference to FIGS. 1 and 2 which are a schematic representation of the knee joint as seen from the medial or lateral side, and in a perspective view. As seen there, the tibia includes upper joint load-bearing surfaces A which are slightly curved and slope downward in a posterior direction relative to the longitudinal axis of the tibia. The femur includes lateral and medial condyles whose load-bearing surface outlines B can be approximated by circular arcs. That is, the centers of curvature C of those portions of the load-bearing surface which are in contact with the tibia at various angles of flexure are not identical. As seen in FIG. 1, at small degrees of flexion the arc which is defined by the load-bearing surface has an instantaneous center of curvature C. However, at greater flexion of the knee the arc defined by the load-bearing surface has an instantaneous center of curvature C' which is different from the previously mentioned arc. Instantaneous centers of curvature C to C', through which centers an axis of rotation of the knee joint undergoes, indicates an instantaneous center of curvature only for the specified arc of motion. The path of the serial locations of the instantaneous centers of curvature during flexion-extension of the knee joint is called the evolute. All movements of the centers of rotation differ from knee to knee and from the medial to the lateral sides of a given knee. In many practical clinical situations, it is necessary to make simple estimates of the location of the axis of rotation of the knee joint. A series of radiographs is required to precisely identify the instantaneous axis of rotation at a knee joint. This method is not practical in ordinary clinical situations. However, according to recent developments in the area of knee kinematics it has been discovered that "one" axis occurs throughout the most arc of motion. The review of the development of concepts of knee kinematics is disclosed in publication "Development of the concepts of knee kinematics" by Smith P N et al, published 2003 December; 84(12): 1895-902, where the derivation of the flexion-extension axis by using 3-dimensional imaging technology was applied. According to said review, "one" posterior condylar axis is effective from 15° to 150° of the knee flexion. This axis passes through the origins of the medial (MCL) and lateral collateral ligaments (LCL) and passes through the intersection of the cruciate ligaments. It closely approximates the epicondylar line and is offset from the sagittal plane by 7°. Further, in said publication the description of the screw-home mechanism can be overcome by external forces during active movement. Additionally, cited authors Blankevoort et al and La Fortune et all found no evidence of screw-home mechanism in vivo. In conclusion of the said publication, the model of the knee as a ball-and-socket joint is a model in which the knee can function. Further, it is recommended to the designers of knee prosthesis not to apply a roll back design but rather to incorporate freedom or control of longitudinal rotation, which recommendation has been incorporated in the present invention, particularly freedom of longitudinal rotation.

The concept of rolling one surface on another was utilized in the structure disclosed in "Restoration of Function in the Knee and Elbow with a Hinge Distractor Apparatus" by Volkov et al (see The Journal Of Bone and Joint Surgery, Vol. 57-A, No. 5, July 1975, pp. 591 to 600). In the design there described, two transverse pins through the femur and tibia held an adjustable rack and pinion on the medial and lateral sides as well as a locking mechanism anteriorly. Traction bows encircled the anterior halves of the shank and thigh. The rack and pinion arrangement utilized the concept of rolling one surface on another. However, this design was complex and did not accurately approximate the motion of the knee. The rack and pinion resulted in backward motion of the femoral condyles on the tibial condyles during flexion. Moreover, there were no differences in motion between the medial and lateral sides of the joint.

The prior art document published under no. WO2011049796 on Apr. 28, 2011 is directed to the implantable assemblies for manipulating energy transferred by means of flexing absorbing members, wherein said means are configured to flex and absorb energy transferred by the members of the anatomical joint. Document no. US2004260302 published on Dec. 23, 2004 discloses an internal brace for distraction arthroplasty, the internal brace includes femoral and tibial components which can be fixed to the patient's femur and tibia and which in combination distract or separate the knee joint without substantially hindering mobility of the knee. The invention provides an implantable brace for use in a knee joint, the implantable brace functions as a wedge in this meniscal space to distract or to open the joint where there has been unicompartment articulate cartilage narrowing, while enabling motion of the knee both in anterior and posterior rolling motions and providing for rotational and sagittal plane motion.

None of the prior art documents is directed to a device intended for temporary distracting the knee joint and at the same time to allow mobility of the anatomical joint.

It is an object of the present invention to provide an external load-bearing distracting device for the knee joint which distracts the knee joint and unloads the knee cartilage while positively enabling natural motion of the knee and bearing a required portion of the load.

Another object of the present invention is to provide an external load-bearing distracting device for the knee joint which provides flexion-extension of the knee joint in the range at least between 0-90°, wherein natural range of motion of the knee joint is not affected, particularly freedom of longitudinal rotation.

Another object of present invention is to provide an external load-bearing distracting device for the knee joint which is temporally attached to the patient, preferably for a period of 6 to 8 weeks, said device is intended for use particularly, but not exclusively, in relation to treatment of osteoarthritis (OA), focal cartilage defects and treatment of fractures occurred inside the knee joint, wherein a reduction of subsequent motion of the joint, after removal the distracting device, is prevented.

SUMMARY OF THE INVENTION

The present invention provides an external load bearing distracting device for an articulating anatomical joint. The external load bearing distracting device comprising a first component configured to be attached to a first anatomical member of an articulating anatomical joint ("first translational insert"), a second component operably associated with the first component ("first rotatable extension"); a third component configured to be attached to a second member of the articulating anatomical joint ("second translational insert"), a fourth component operably associated with the third component ("second rotatable extension"); retaining components ("retainers"); a means for adjusting and fixing the first component and the third component at desired longitudinal position in relation to a flexion-extension axis of rotation of the articulating anatomical joint; and a joint joining the first and second rotatable extensions, wherein the joint is configured to enable six degrees of motion of the articulating anatomical joint. Each of said four components is carried out of one solid part, the first and second translational inserts are slidably and telescopically interconnected within the first and second rotatable extensions, respectively. Each of the first and second rotatable extensions is disposed on the mutually opposite side in relation to the mediolateral axis of the joint, and each comprises one retainer. Each of the first and second translational inserts comprises the means for adjusting and fixing the first and second translational inserts at the desired longitudinal position in relation to a flexion-extension axis of rotation of the articulating anatomical joint, the means for adjusting and fixing the first and second translational inserts being positioned inside the respective retainers of the first and second rotatable extensions. Each retainer has the shape of a hollow frame. A segment of the first translational insert is slidably and telescopically arranged inside the first rotatable extension, and a segment of the second translational insert is slidably and telescopically arranged inside the second rotatable extension, where all said components are capable of rotating around a mediolateral axis simultaneously, and the first and second translational insert are capable of axially moving along the longitudinal axis; wherein the first and second rotatable extensions each comprises the retainer operably associated with the means for adjusting and limiting axial movement of the first and second translational inserts. Each central part of the first and second translational inserts is provided with an external threaded portion, where on each external threaded portion are arranged the means for adjusting and fixing the first and second translational inserts at the desired longitudinal position, the means are one pair of nuts. Each pair of nuts is positioned inside the respective retainer of the first and second rotatable extensions. By virtue of both pair of nuts and both retainers, the first and second translational inserts is each held at the desired longitudinal position providing distraction of the articulating anatomical joint.

In some preferable embodiments of the present invention, the first and second rotational extensions are each provided with the retainer. Each retainer is arranged on the proximal end of the first and second rotatable extensions. In this embodiment of the present invention, a segment of the first translational insert is slidably and telescopically arranged inside the first rotatable extension, and a segment of the second translational insert is slidably and telescopically arranged inside the second rotatable extension, where all said components are capable of rotating around a mediolateral axis. The first and second translational inserts are both provided with the means for adjusting and fixing the first and second translational inserts at the desired longitudinal position in relation to a flexion-extension axis of rotation of the articulating anatomical joint. Each central part of the first and second translational insert is provided with an external threaded portion, where on each external threaded portion are arranged the means for adjusting and fixing the first and second translational inserts at the desired longitudinal position in relation to a flexion-extension axis of rotation of the articulating anatomical joint, the means are one pair of nuts. Each pair of nuts is positioned inside the respective retainer of the first and second rotatable extensions. By virtue of both pair of nuts and both retainers, the first and second translational inserts is are each held at the desired longitudinal position providing distraction of the articulating anatomical joint. Further, as well as described in first variant of the present invention, the joint is joining the first and second rotatable extensions, wherein the joint is configured to enable six degrees of motion of the articulating anatomical joint. Replacement of position and arrangement of the retainers and of the means for adjusting and fixing the first and second translational inserts at the desired longitudinal position in relation to a flexion-extension axis of rotation of the articulating anatomical joint presents another way of carrying out the invention and does not in any way affect the functionality of the invention.

In a preferred embodiment of the present invention the articulating anatomical joint is a knee joint, where said first translational insert is adapted to be fixed to a femur of the knee joint and said second translational insert is adapted to be fixed to a tibia of the knee joint.

In one embodiment of the present invention the joint joining the first and second rotatable extensions comprises a structure like a ball-and-ring joint.

In another embodiment of the present invention the joint joining the first and second rotatable extensions comprises a structure having mutually connected a ball bearing and a cardan joint.

In both of the embodiments the joint enables natural movement of the knee joint, thus preventing a consequent shortening of the soft tissue structures resulting in loss of motion of the knee joint after the distracting device is removed.

Depending on the position of a degenerated articular cartilage surfaces, the external load bearing distracting device can be anchored at a lateral or at a medial side of the articulating anatomical joint, or simultaneously on both sides of the articulating anatomical joint.

BRIEF DESCRIPTION OF THE DRAWINGS

Various other objects, features and attendant advantages of the present invention will be more fully appreciated as the same become better understood from the following detailed description when considered in connection with the accompanying drawings in which like reference characters designate like or corresponding parts throughout the several views and wherein.

DETAILED DESCRIPTION OF THE PREFERRED EMBODIMENTS

Although the knee joint is being described here, it is contemplated that these devices can also be placed at other articular, cartilaginous joints throughout the body, and some non-articular, non-cartilaginous joints that are capable of motion in a flexion/extension direction that exceeds forty-five degrees. As best seen in FIG. 1, the tibia load bearing surface A is simulated as a planar surface while the femoral condylar load bearing surfaces are simulated as circular load bearing surfaces B having centrodes moving from point 1 to point 4 during the flexion of the knee. That is, it has been determined that the rolling and sliding motion of the knee joint causes the centrode to move from 1 to 4 during flexure, the distance 1-4 varying between the lateral and medial compartments. According to the recent developments in in the area of knee kinematics it has been detected as screw-home mechanism is based on 2-dimensional passive models, and in addition authors Bankevoort et al and La Fortune et al found no evidence of screw-home mechanism in vivo. Instead, "one" posterior condylar axis is effective from 15° to 150° of knee flexion, hereafter referring to a flexion-extension axis of the knee joint. Thus, the present invention attempts to provide a device which enables natural movement of the knee joint and distracts the knee joint in a longitudinal direction (in a sagittal plane) to the distance corresponding at least to a healthy knee joint. Distracting the knee joint to distance corresponding at least to the healthy knee joint, for a period of time determined by the medical indications, enables recovery of the cartilage defects related to various knee joint diseases or injuries. In a knee distraction surgery, femur and tibia bones are slightly pulled apart and held into place by a plurality of pins which protrude from the skin in an external fixation, where a joint of an external load bearing distracting device enables natural movement of the knee joint. Patient wear the distraction device for 6 to 8 weeks to allow cartilage to regenerate. With the bone-on-bone alleviated—the articular cartilage can now repair itself without the weight and mechanical stress of the "bone on bone". The knee distraction procedure can be combined with other knee treatments such as applying treatment with hyaluronic acid or stem cells treatment for cartilage tissue regeneration, or injecting signaling molecules or any other local or systemic treatment of the knee joint.

The present invention distracts the load bearing surfaces A and B by providing an external load bearing distracting device mounted to the lateral or medial sides of a tibia and a femur, possibly by transcutaneous transverse pins.

It must be noted that as used herein and in the appended claims, the singular forms "a", "an", and "the" include plural referents unless the context clearly dictates otherwise. Thus, for example, reference to "a means" or "the means" includes plurality of such means.

Reference to the term "distal" associated with components of the present invention relates to a part of the component situated away from the flexion-extension axis of rotation of the articulating anatomical joint or respectively the joint according to the present invention, and reference to the term "proximal" associated with components of the present invention relates to a part of the component situated nearer to the flexion-extension axis of rotation of the articulating anatomical joint or respectively the joint according to the present invention.

Referring now to the drawings, which are provided by way of example and not limitation, the present invention is directed towards a device for distraction of an articulating anatomical joint with the function of eliminating weight and mechanical stress of the physiological load in a damaged anatomical joint for a limited period of time. Whereas the present invention is particularly suited to address issues associated with osteoarthritis (OA), focal cartilage defects and treatment of fractures occurred inside the knee joint, but also the present invention lends itself to broader applications.

Figure 3:
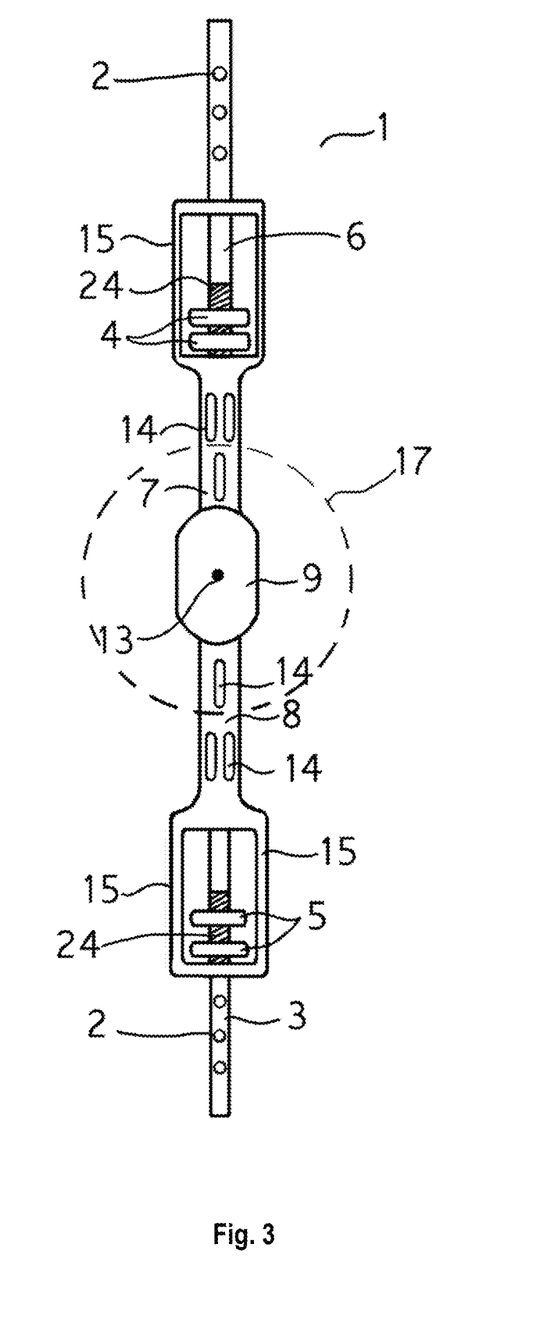
FIG. 3 is a schematic illustration from the side view of a distracting device according to one embodiment of the present invention.
Figure 4:
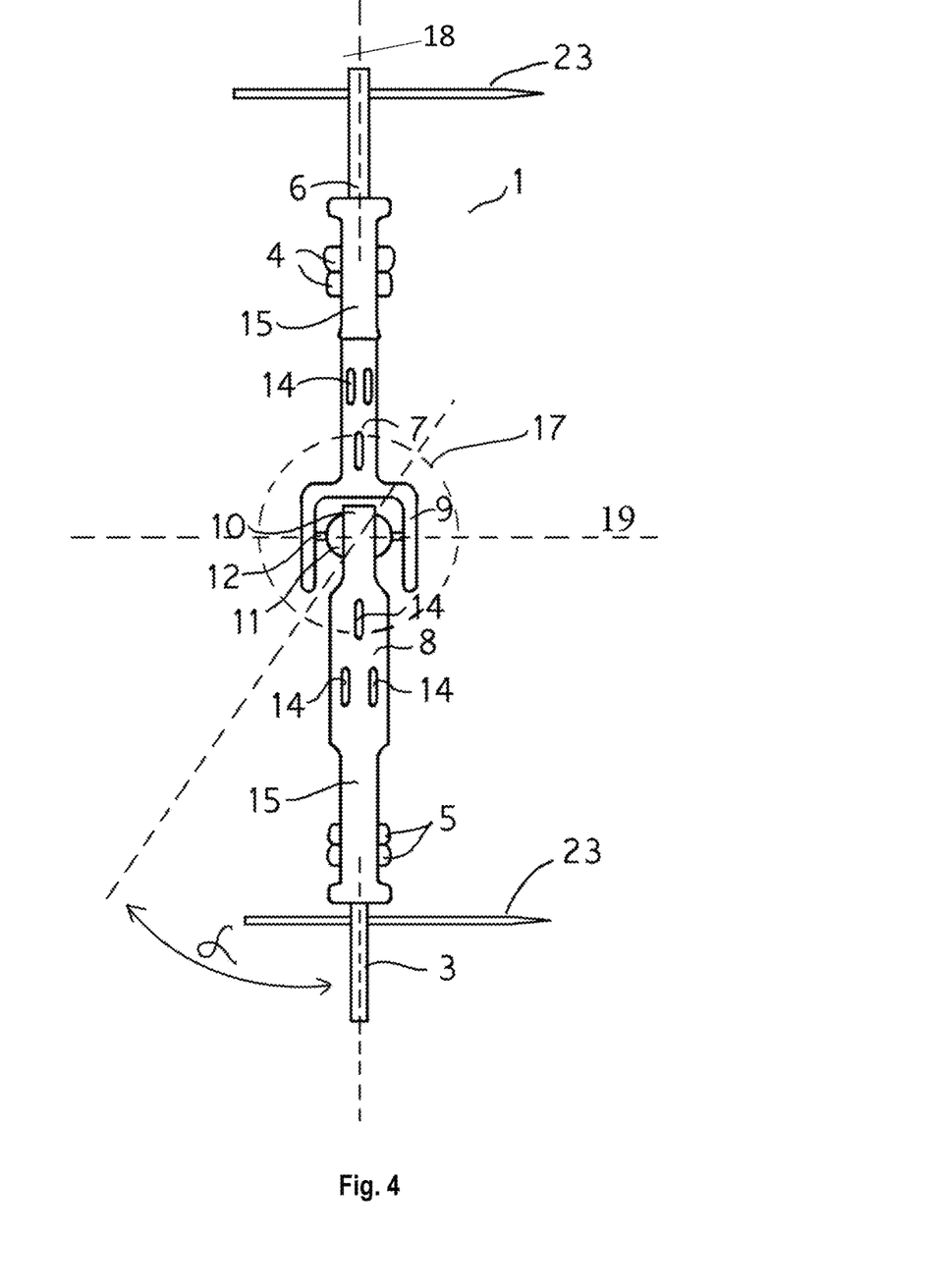
FIG. 4 is front view of a distracting device from the FIG. 3.

Referring to FIGS. 3 and 4, an external load bearing distracting device 1 for an articulating anatomical joint comprising a first translational insert 6 configured to be attached to a first anatomical member of the articulating anatomical joint and a first rotatable extension 7 operably associated with the first translational insert 6; a second translational insert 3 configured to be attached to a second member of the articulating anatomical joint, and a second rotatable extension 8 operably associated with the second translational insert 3; and a joint 17 joining the first and second rotatable extensions 7, 8 are shown. Said components 6, 7, 3 and 8 are disposed along a longitudinal axis 18 in the extension of each other, a segment of the first translational insert 6 is slidably and telescopically arranged inside the first rotatable extension 7 and a segment of the second translational insert 3 is slidably and telescopically arranged inside the second rotatable extension 8. Said segments are positioned at proximal ends of the first and second translational inserts 6, 3. Each of said four components 6, 7, 8 and 3 is preferably carried out of one solid part. The first and second translational inserts 6, 3 are rods having round cross section whose distal ends are configured to be attached to the first and respectively to the second anatomical member of the articulating anatomical joint. Distal ends of said first and second translational inserts 6, 3 are provided with a plurality of perforations 2, through which perforations 2 transcutaneous transverse pins 23 secure the first translational insert 6 to femur and respectively the second translational insert 3 to tibia to medial or lateral sides of the anatomical articulating joint. Preferably, the perforations 2 are spaced apart as far as is practical in order to provide maximum rigidity in the connection between the components 6 and 3 and corresponding bones. The transcutaneous pins 23 are formed of metal and are of a type which is well known in the art. Each central part of the first and second translational inserts 6, 3 is provided with an external threaded portion 24, where on each of the external threaded portions 24 is provided a pair of nuts 4 and 5.

The first and second rotatable extensions 7, 8, within which the first and second translational inserts 6, 3 are arranged and are capable of sliding along the longitudinal axis 18, are carried out as hollow bodies, preferably in the form of tubes. In another embodiment, the first and second rotatable extensions 7, 8 may be carried out as guide rails having profile such as C profile or round C profile, and the first and second translational inserts 6, 3 are carried out as corresponding sliding rails. Depending on the guide rails profile, the first and second translational inserts 6, 3 may be rods having round cross section, or may have another cross-section at their proximal end that is slidably arranged inside or along the first and second rotatable extensions 7, 8, respectively. The first and second rotatable extensions 7, 8 each comprise a retainer 15 for limiting axial longitudinal movement of the first and second translational inserts 6, 3 inside the first and second rotatable extensions 7, 8. Each retainer 15 is arranged at distal end of the first and second rotatable extensions 7, 8. The retainer 15 is carried out as a widening and is constituent part of the first and second rotatable extensions 7, 8, respectively. The retainer 15 has the form of a hollow frame of a rectangular or the like shape, where each retainer 15 at its upper (distal) and its lower (proximal) end is provided with orifices through which the first and second translational inserts 6, 3 undergo and slide inside or along said first and second rotatable extensions 7, 8, respectively. Cross-section of said orifices is correlated to the cross-sections of the first and second translational inserts 6, 3. In the embodiment where the first and second rotatable extensions 7, 8 are carried out as guide rails, segments of the first and second translational inserts 6, 3 at their proximal ends are carried out as rails and their central parts and distal ends are carried out as rods having round cross section whose distal ends are configured to be attached to the first and respectively to the second anatomical member of the articulating anatomical joint. Central parts of the first and second translational inserts 6, 3 are provided with an external threaded portion. Cross-section of the orifice positioned at the upper end of the retainer 15 correlates to the cross-section of distal ends of the first and second translational inserts 6, 3, and cross-section of the orifice positioned at the lower end of the retainer 15 correlates to the cross-section of the proximal ends of the first and second translational inserts 6, 3 carried out as rails.

Figure 5:
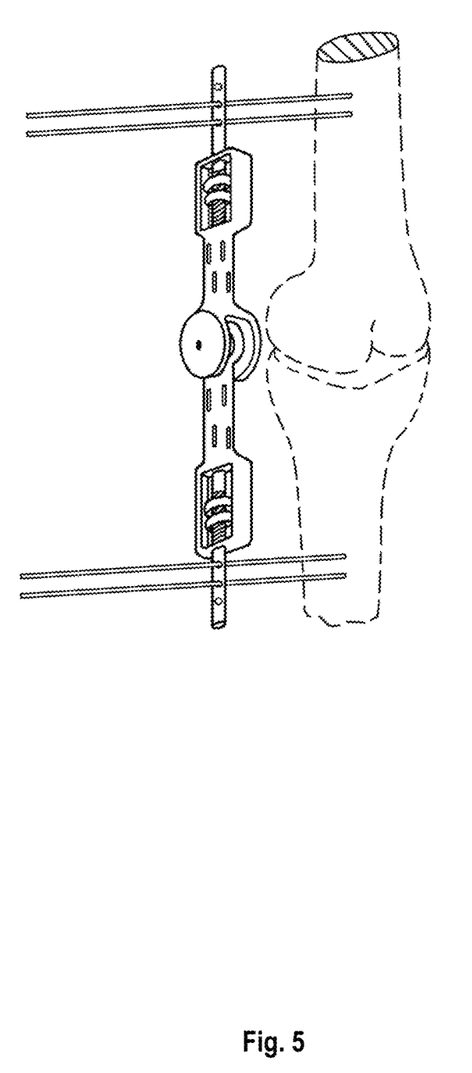
FIG. 5 is a perspective view showing the distracting device anchored to a knee joint.

Said each retainer 15 is disposed at distal end of the first and second rotatable extensions 7, 8, where each retainer 15 has dimensions that restricts axial longitudinal movement of the first and second translational inserts 6, 3 by the virtue of the pair of threaded nuts 4 and respectively 5, where each pair of threaded nuts 4 and 5 is arranged at the external threaded portion 24 of the first and second translational inserts 6, 3, where each threaded portion 24 and corresponding pair of threaded nuts 4 and 5 are positioned inside the corresponding retainer 15 of the first and second rotatable extension 7, 8. By means of both respective retainers 15, each pair of threaded nuts 4 and 5 is supported and held at desired longitudinal position. The retainer 15 defined by the rectangular-like shape enables access to each pair of threaded nuts 4 and 5 in order to adjust the longitudinal position of the first and second translational inserts 6, 3 within the first and second rotatable extensions 7, 8, respectively, thus ensuring that the articulating anatomical joint is continually distracted. FIG. 5 illustrate the distracting device 1 installed on the lateral side of a knee joint. A mediolateral axis 19 of rotation of the joint 17 is aligned with the flexion-extension axis of rotation of the articulating anatomical joint. After attaching the first translational insert 6 to femur and the second translational insert 3 to tibia, each pair of threaded nuts 4, 5 is positioned respectively on associated first or second translational insert 6, 3 such that each pair of nuts 4, 5 bears against its associated retainer's 15 the inner surface proximal to the joint 17. By screwing respective pair of threaded nuts 4 and 5, the first and second translational inserts 6, 3 are shifted along the longitudinal axis 18 in opposite direction. By shifting the first and second translational inserts 6, 3 away from the mediolateral axis 19 of the joint 17, femur and tibia are mutually distracted to distance corresponding at least to a healthy knee joint. After attaching the distracting device 1 to the user and unloading the joint cartilage by positioning the threaded nuts 4, 5 on the translational inserts 6, 3, during the user's natural joint motion as the translational inserts 6, 3 slide within the rotatable extensions 7, 8, each pair of nuts 4, 5 may contact the sides of each retainer 15, limiting translational movement in that direction. As depicted in FIGS. 3 and 5, each pair of nuts may be positioned with some distance therebetween, or a nut may be positioned directly adjacent to its counterpart, as depicted in FIG. 4.

Referring to FIGS. 3, 4, 6 and 7, according to one embodiment of the present invention, a proximal end of the second component 7 forming the joint 17 is provided with a "yoke" coupling link 9. Within the coupling link 9 a ball member 11 is arranged and fixed to hooks 25 of the coupling link 9 by means of a cross shaft 12. Throughout the hooks 25 of the coupling link 9, the ball member 11 and the cross shaft 12 is arranged a bore 13. The bore 13 is arranged in the center of rotation of the joint 17. The center of rotation of the joint 17 is mediolateral axis 19. The bore 13 enables the positioning the mediolateral axis 19 of the joint 17, by the virtue of the Kirschner wire, to be aligned with the flexion-extension axis of the articulating anatomical joint. The distracting device 1 is anchored in a position where the mediolateral axis 19 of the joint 17 corresponds to the flexion-extension axis of rotation of the articulating anatomical joint, the flexion-extension axis is determined to enable flexion-extension of the articulating anatomical joint for at least 90°. The bore 13 is dimensioned to allow Kirschner wire to pass therethrough.

Figure 6:
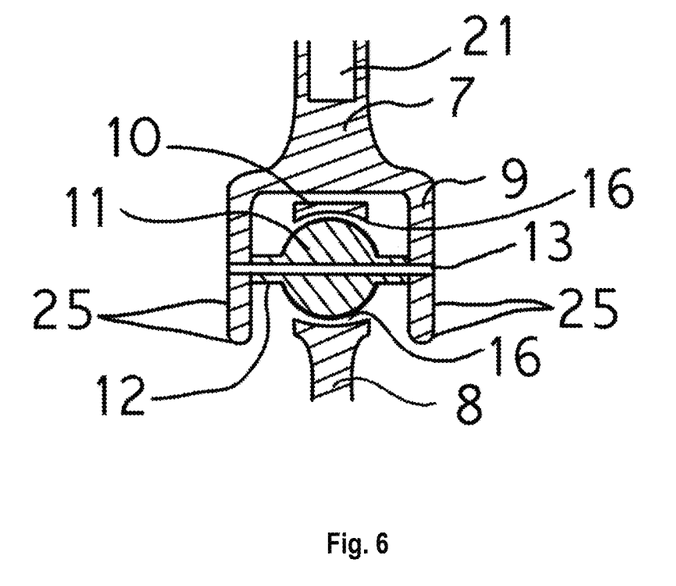
FIG. 6 is a cross section view from the front side of a joint according to one embodiment of the present invention.
Figure 7:
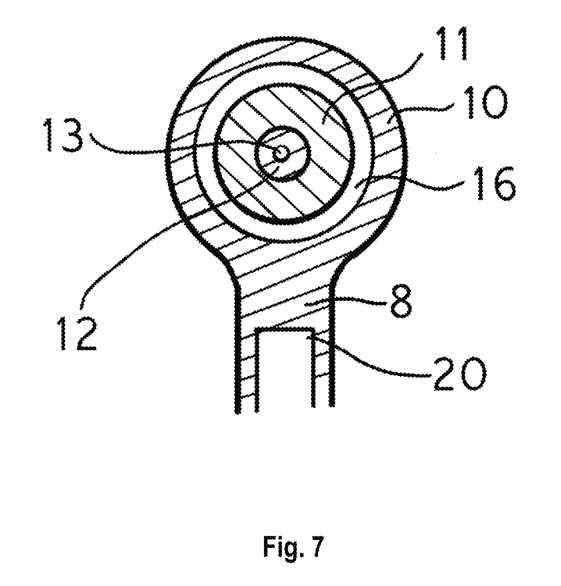
FIG. 7 is a cross section view of the joint from FIG. 6 from the lateral side.

A proximal end of the second rotatable extension 8 forming the joint 17 is a ring-shaped member 10 embracing the ball member 11, whereby the first and second rotatable extensions 7, 8 enable rotation and flexing of the articulating anatomical joint. Referring to FIGS. 6 and 7, between the ring-shaped member 10 and the ball member 11 is arranged a gap 16. The gap 16 enables additional "slight" medial-lateral translation of the second rotatable extension 8 relative to the first rotatable extension 7. Referring to FIG. 4, the second rotatable extension 8 is able to be inclined for an angle α in respect to the longitudinal axis 18. In addition, the second rotatable extension 8 is able to simultaneously revolve around the longitudinal axis 18. By this feature the distracting device 1 incorporates freedom of longitudinal rotation. The value of the angle α is determined by the length of the hooks 25 of the coupling link 9 and as well by the dimension of the gap 16. The value of the angle α is preferably such to enable abduction-adduction rotation and simultaneous internal-external rotation of the second member of the anatomical joint in respect of the first anatomical member of an articulating anatomical joint. In the preferred embodiment of the invention, the value of the angle α is such that enables said rotations of any knee, irrespective of the individual knee.

Figure 8:
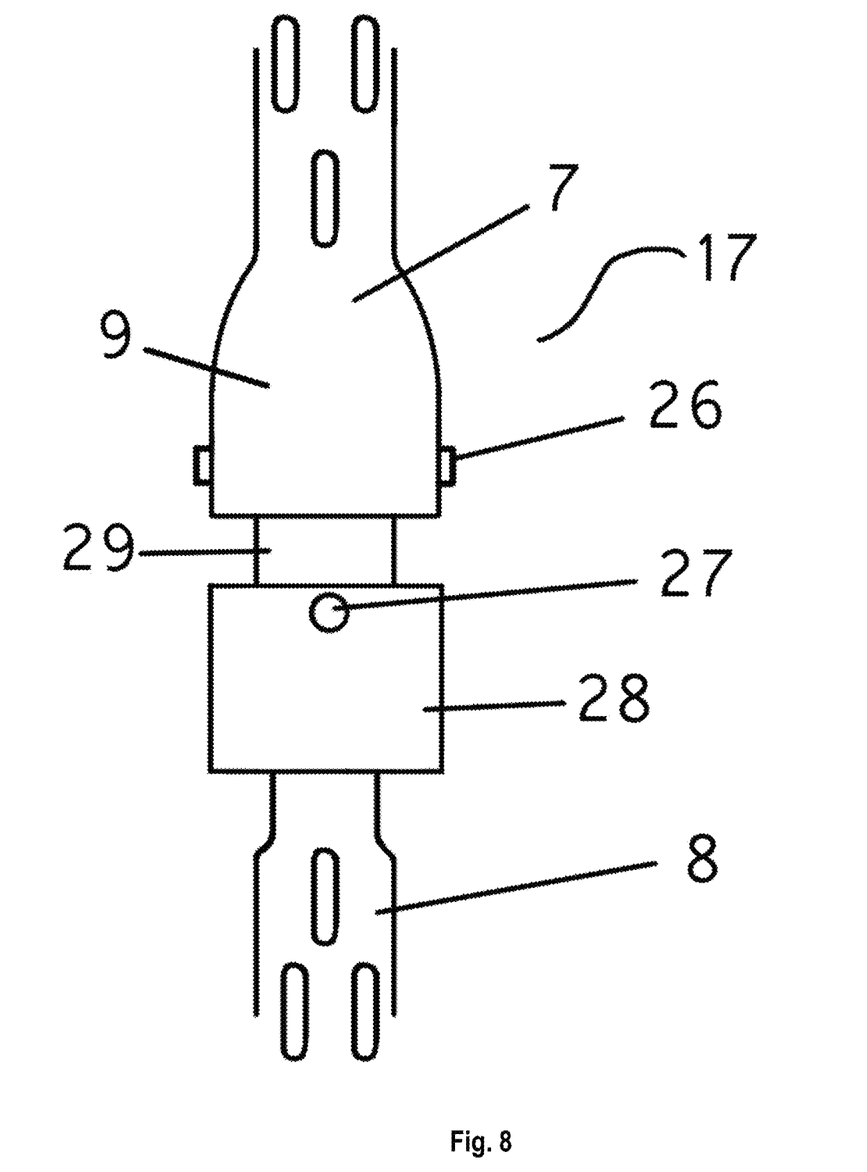
FIG. 8 is a schematic illustration from the front view of a joint according to another embodiment of the present invention.
Figure 9:
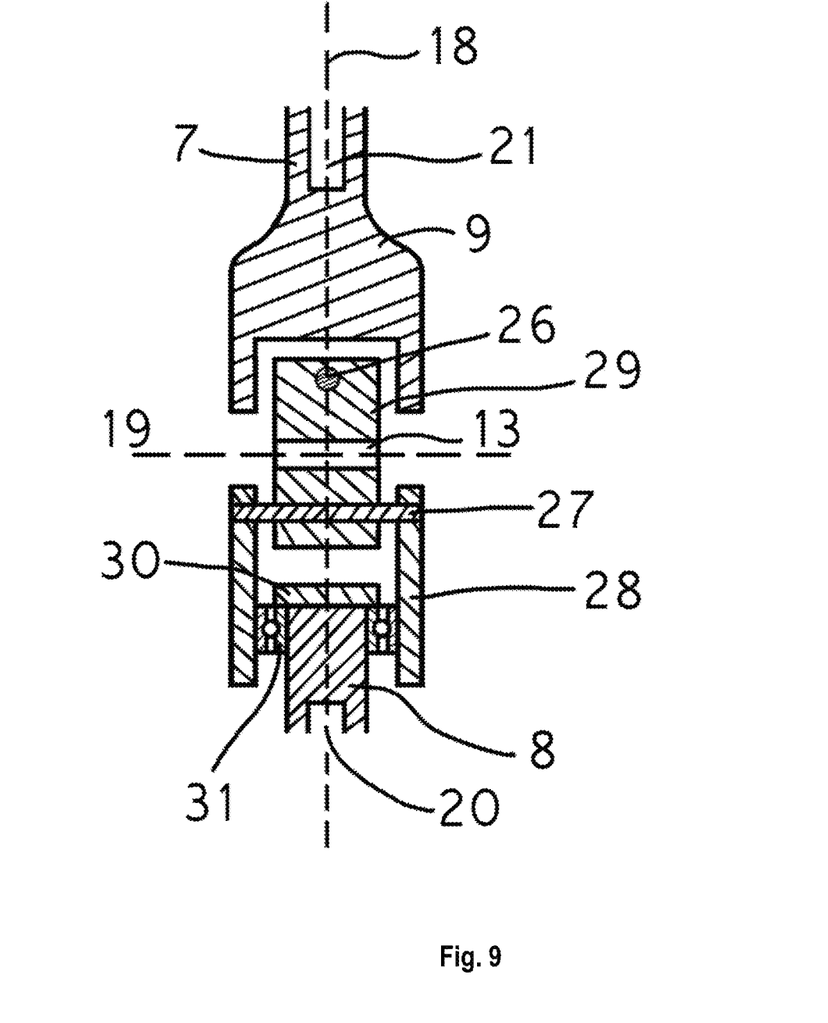
FIG. 9 is a cross section view of the joint from FIG. 8 from the front side.

According to another embodiment, the joint 17 is carried out by means of a cardan joint coupled to the second rotatable extension 8 by means of a ball bearing 31. Referring to FIGS. 8 and 9, the joint 17 comprises a cylinder having a "yoke" coupling link 9 arranged at proximal end of the first rotatable extension 7. The coupling link 9 is connected to a center block 29 of the cardan joint by virtue of a first pin 26. The first pin 26 undergoing the center block 29 and the coupling link 9 is positioned at an upper part of the center block 29, the upper part of the center block 29 is arranged inside the coupling link 9. By the means of the first pin 26, abduction-adduction rotation of the second rotatable extension 8 relative to the first rotatable extension 7 by the angle α is provided (angle α is not shown in the FIG. 9). At the lower part of the center block 29 is arranged a second pin 27. The second pin 27 is perpendicular in respect to the first pin 26 and connects the center block 29 to a second coupling link 28 so that the second coupling link 28 is able to rotate around an axis of the second pin 27 whereby providing rotation of the second rotatable extension 8 relative to the first rotatable extension 7, whereby flexion-extension of the second member of the anatomical joint in respect of the first anatomical member of an articulating anatomical joint is provided. The second coupling link 28 is connected to the ball bearing 31, the ball bearing is arranged at the proximal end of the second rotatable extension 8 in a manner that the second rotatable extension 8 rotates around the longitudinal axis 18, whereby internal-external rotation of the second member of the anatomical joint in respect of the first anatomical member of an articulating anatomical joint is provided. An outer ring of the ball bearing 31 is firmly connected to interior round surface of the second coupling link 28, and an inner bore of the ball ring 31 is firmly connected to an outer round surface of the second rotatable extension 8. Further, the ball bearing 31 is secured to the proximal end of the second rotatable extension 8 by a mean 30. The mean 30 can be nut or by any fixing means well known in the art. Further, the center block 29 is provided with a bore 13, wherein the bore 13 enables the positioning of the joint 17, by the virtue of the Kirschner wire, in the flexion-extension axis of rotation of the articulating anatomical joint enabling its flexion-extension. The bore 13 can be arranged to pass through the second pin 27. The bore 13 is dimensioned to allow Kirschner wire to pass therethrough.

Figure 10:
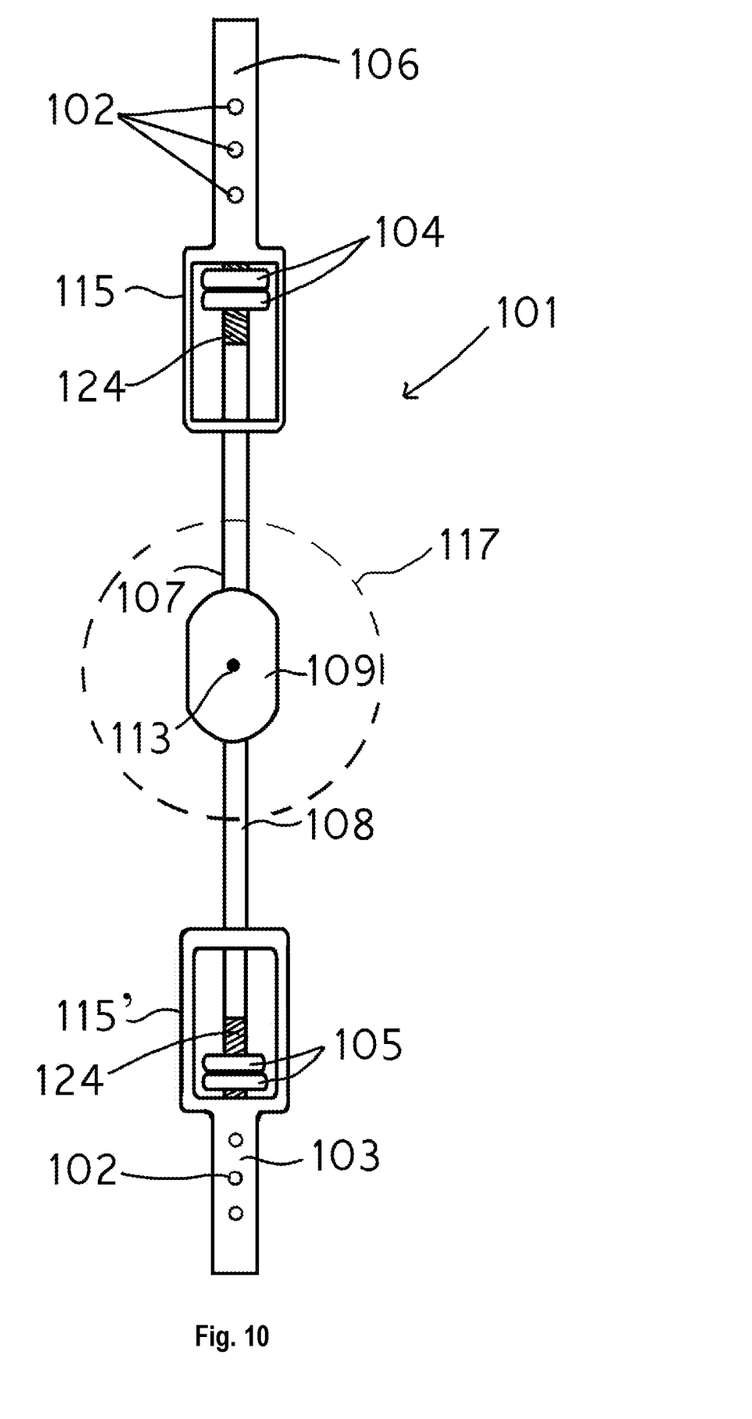
FIG. 10 is a schematic illustration from the side view of a distracting device according to a second embodiment of the present invention.
Figure 11:
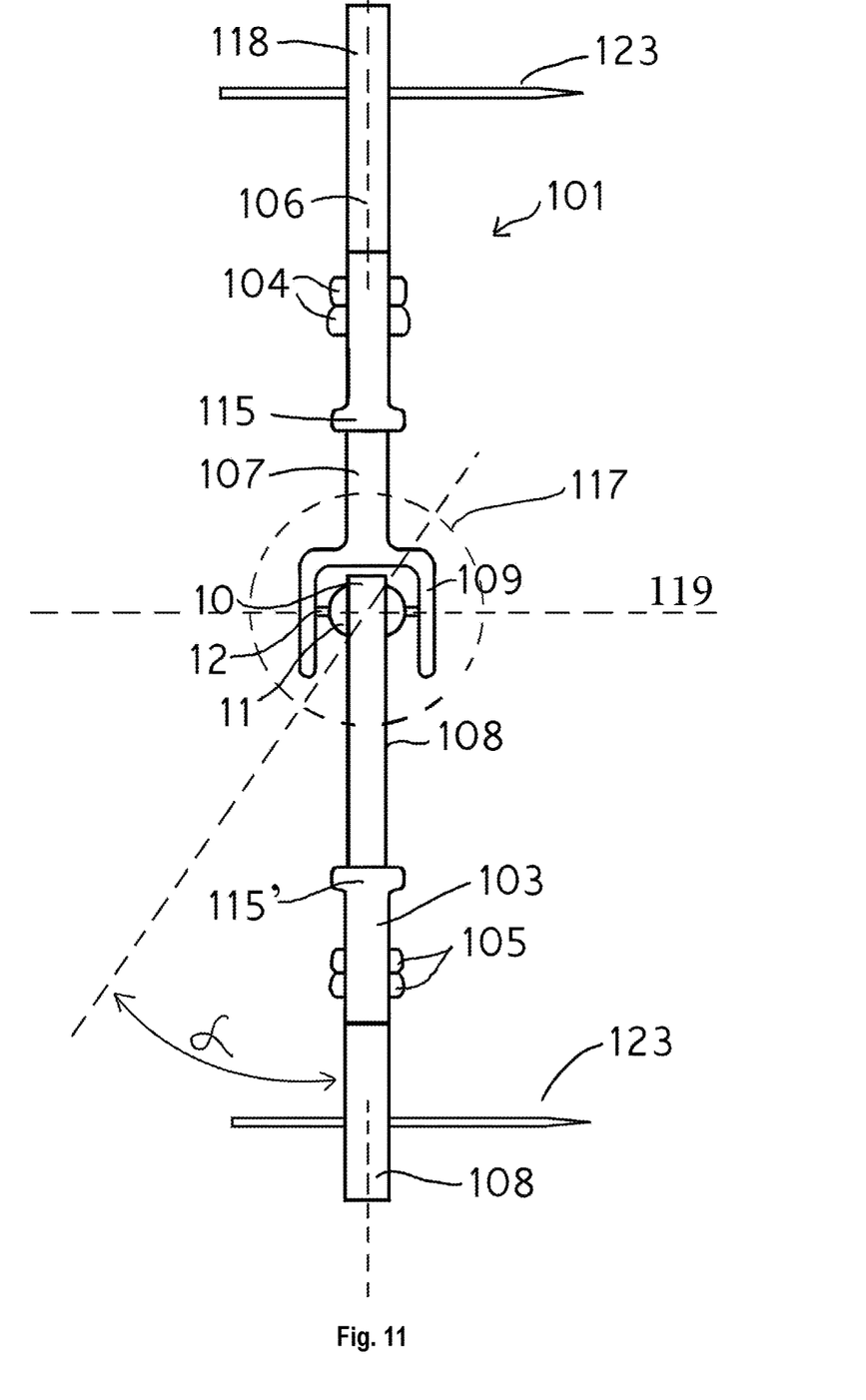
FIG. 11 is a front view of the distracting device of FIG. 10.

In a second embodiment of the present invention, shown in FIGS. 10 and 11, the retainers 15 seen in the embodiment shown in FIGS. 3 and 4 are provided on the first translational insert 6 and second translational insert 3 instead of on the first rotatable extension 7 and the second rotatable extension 8. A longitudinal displacement of the first translational insert 6 relative to the first rotatable extension 7 is limited by contact between the first pair of nuts 104 and the first retainer 115 and a longitudinal displacement of the second translational insert 3 relative to the second rotatable extension 8 is limited by contact between the second pair of nuts 105 and the second retainer 115'. Referring now to FIGS. 10 and 11, an external load bearing distracting device 101 for an articulating anatomical joint comprises a first translational insert 106 configured to be attached to a first anatomical member of an articulating anatomical joint and a first rotatable extension 107 is operably associated with the first translational insert 106. A second translational insert 103 is configured to be attached to the second member of the articulating anatomical joint, and a second rotatable extension 108 is operably associated with the second translational insert 103. A rotating joint 117 joins the first and second rotatable extensions 107, 108. The components 106, 107, 103 and 108 are disposed along a longitudinal axis 118 in the extension of each other. The retainers 115 and 115' are arranged at the proximal ends of the first and second translational inserts 106, 103. Specifically, retainer 115 is provided at the lower end of the first translational insert 106 and another retainer 115' is provided at the upper end of the second translational insert 103. A segment of the first rotatable extension 107 is slidably and telescopically arranged inside the first translational insert 106, and a segment of the second rotatable extension 108 is slidably and telescopically arranged inside the second translational insert 103. Said segments are positioned at distal ends of the first and second rotatable extensions 107, 108. Each of said four components 106, 107, 108 and 103 is preferably carried out of one solid part. Each central part of the first and second rotatable extensions 107, 108 is provided with an external threaded portion 124, where on each of the external threaded portion 124 is arranged one pair of threaded nuts 104 and 105, where each pair of threaded nuts 104 and 105 is positioned inside the respective retainer 115, 115' of the first and second translational inserts 106, 103. By means of both retainers 115, 115' each pair of threaded nuts 104 and 105 is supported and held at the desired longitudinal position providing distraction of the articulating anatomical joint. Distal ends of the first and second translational inserts 106, 103 each have a shape of a hollow body, preferably in a form of a tube whose distal ends are provided with a plurality of perforations 102, and the first and second rotatable extensions 107, 108 are rods having round cross section. Each retainer 115, 115' has the shape of a hollow frame of the rectangular or a like shape. Further, each retainer 115, 115' at its upper and lower end is provided with orifices, through which orifices the first and second rotatable extensions 107, 108 undergoes and slides inside the first and second translational inserts 106, 103, respectively. Cross-section of said orifices is correlated to the cross-sections of the first and second rotatable extensions 107, 108.

In another embodiment, the first and second translational inserts 106, 103 may be carried out as guide rails having profile such as C profile or round C profile, and the first and second rotatable extensions 107, 108 are carried out as corresponding sliding rails. Depending on the guide rails profile, the first and second rotatable extensions 107, 108 may be rods having round cross section or may have another cross-section at their distal end that is slidably arranged inside or along the first and second translational inserts 106, 103, respectively.

In the embodiment where the first and second translational inserts 106, 103 are carried out as guide rails, segments of the first and second rotatable extensions 107, 108 at their distal ends are carried out as rails and their central parts and distal ends are carried out as rods having round cross section. Distal ends of the first and second translational inserts 106, 103 are configured to be attached to the first and respectively to the second anatomical member of the articulating anatomical joint. Central parts of the first and second rotatable extensions 107, 108 are provided with an external threaded portion. Cross-section of the orifice positioned at the upper end of the retainer 115, 115' correlates to the cross-section of distal ends of the first and second rotatable extensions 107, 108 components carried out as rails, and the cross-section of the orifice positioned at the lower end of the retainers 115, 115' correlates to the cross-section of the proximal ends of the first and second rotatable extensions 107, 108.

Components of the distracting device 1, 101 are made from a metal such as stainless steel or titanium alloy, cobalt chromium alloy, or ceramic or are preferably formed from a high strength polymer material such as RCH 1000 high molecular weight polyethylene or Hi-Fax 1900 ultra-high molecular weight polyethylenes to minimize friction and wear. Combinations of materials can also be used to maximize the properties of materials for different components of the present invention. The transcutaneous pins 23, 123 are formed of metal and are of a type which is well known in the art.

Obviously, numerous modifications and variations of the present invention are possible in light of the above teachings. It is therefore to be understood that within the scope of the appended claims, the invention may be practiced otherwise than as specifically described herein.

The invention claimed is:

1. An external load bearing distracting device for an articulating anatomical joint comprising:
a first translational insert configured to be attached to a first anatomical member of the articulating anatomical joint;
a first rotatable extension comprising a first retainer;
a second translational insert configured to be attached to a second member of the articulating anatomical joint;
a second rotatable extension comprising a second retainer;
a joint joining the first and second rotatable extensions; the joint being configured to enable natural motion present in the articulating anatomical joint;
a first pair of threaded nuts provided on an externally threaded portion of the first translational insert; and
a second pair of threaded nuts provided on an externally threaded portion of the second translational insert;
wherein the first translational insert is slidably and telescopically interconnected with the first rotatable extension, and the second translational insert is slidably and telescopically interconnected with the second rotatable extension,
the first and second rotatable extensions are configured to be disposed on opposite sides of the mediolateral axis of the joint, and
the first pair of nuts is positioned within the first retainer of the first rotatable extension and the second pair of nuts is positioned within the second retainer of the second rotatable extension such that a longitudinal displacement of the first translational insert relative to the first rotatable extension is limited by contact between the first pair of nuts and the first retainer and a longitudinal displacement of the second translational insert relative to the second rotatable extension is limited by contact between the second pair of nuts and the second retainer.

2. The distracting device according to claim 1, wherein the first retainer is at a distal end of the first rotatable extension and the second retainer is at distal end of the second rotatable extension, the first and second retainers having the shape of a hollow frame.

3. The distracting device according to claim 2, wherein the first and second retainers each has orifices at its upper and lower ends, whereby a proximal end segment of the first translational insert extends through the orifices in the first retainer of the first rotatable extension and a proximal end segment of the second translational insert extends through the orifices in the second retainer of the second rotatable extension.

4. The distracting device according to claim 1, wherein the first and second translational inserts are rods having a round cross section, and a distal end of each of the first and second translational inserts are provided with a plurality of perforations.

5. The distracting device according to claim 4, further comprising one or more transverse pins extending through the perforations in the first and second translational inserts, for attaching the first translational insert to the first anatomical member of the articulating anatomical joint and for attaching the second translational insert to the second anatomical member of the articulating anatomical joint.

6. The distracting device according to claim 5 for use in the treatment of articular cartilage defects in which a new articular cartilage formation of a knee joint is required.

7. The distracting device according to claim 5 for use in the treatment of osteoarthritis (OA), focal cartilage defects and treatment of fractures occurred inside the knee joint.

8. The distracting device according to claim 1, wherein the joint is a ball-and-ring-joint.

9. The distracting device according to claim 8, wherein a proximal end of the first rotatable extension is provided with a yoke link, where within the yoke link a ball member is arranged and fixed to one or more hooks of the yoke link by a cross shaft, wherein a bore extends through the yoke link, the ball member, and the cross shaft.

10. The distracting device according to claim 9, wherein the bore enables the positioning of the joint in the flexion-extension axis of the articulating anatomical joint.

11. The distracting device according to claim 8, wherein a proximal end of the second rotatable extension is a ring-shaped member embracing the ball member, with a gap between the ring-shaped member and the ball member.

12. The distracting device according to claim 1, wherein the joint is a cardan joint.

13. The distracting device according to claim 12, wherein the cardan joint comprises a yoke cylinder having a yoke link arranged at a proximal end of the first rotatable extension, a second yoke link arranged at a proximal end of the second rotatable extension, and a center block connected to the yoke link by virtue of a first pin and to the second yoke link by virtue of a second pin, where the first pin and the second pin are mutually perpendicular.

14. The distracting device according to claim 13, wherein a bore extends through the center block.

15. The distracting device according to claim 13, wherein a bore extends through the second pin.

16. The distracting device according to claim 13, wherein the second yoke link and the second rotatable extension are mutually coupled by a ball bearing.

17. The distracting device according to claim 16, wherein the ball bearing is secured to the proximal end of the second rotatable extension.

18. An external load bearing distracting device for an articulating anatomical joint comprising:
a first translational insert comprising a first retainer and configured to be attached to a first anatomical member of the articulating anatomical joint;
a first rotatable extension;
a second translational insert comprising a second retainer configured to be attached to a second member of the articulating anatomical joint;
a second rotatable extension;
a joint joining the first and second rotatable extensions; the joint being configured to enable natural motion present in the articulating anatomical joint;
a first pair of threaded nuts provided on an externally threaded portion of the first rotatable extension; and
a second pair of threaded nuts provided on an externally threaded portion of the second rotatable extension;
wherein the first translational insert is slidably and telescopically interconnected with the first rotatable extension, and the second translational insert is slidably and telescopically interconnected with the second rotatable extension,
the first and second rotatable extensions are configured to be disposed on opposite sides of the mediolateral axis of the joint, and
the first pair of nuts is positioned within the first retainer of the first translational insert and the second pair of nuts is positioned within the second retainer of the second translational insert such that a longitudinal displacement of the first translational insert relative to the first rotatable extension is limited by contact between the first pair of nuts and the first retainer and a-longitudinal displacement of the second translational insert relative to the second rotatable extension is limited by contact between the second pair of nuts and the second retainer.

19. The distracting device according to claim 18, wherein the first retainer is at a proximal end of the first translational insert and the second retainer is at a proximal end of the second translational insert, the first and second retainers having the shape of a hollow frame.

20. The distracting device according to claim 19, wherein the first and second retainers each has orifices at its upper and lower ends, whereby a proximal end segment of the first rotatable extension extends through the orifices in the first retainer of the first translational insert and a proximal end segment of the second rotatable extension extends through the orifices in the second retainer of the second translational insert.

21. The distracting device according to claim 18, wherein the first and second translational insert each comprises a cylindrical hollow body, a distal end of each of the first and second translational inserts is provided with a plurality of perforations, and at least a segment of each of the first and second rotatable extensions each comprises rods having round cross section.

22. The distracting device according to claim 21, further comprising one or more transverse pins extending through the perforations in the first and second translational inserts for attaching the first translational insert to the first anatomical member of the articulating anatomical joint and for attaching the second translational insert to the second anatomical member of the articulating anatomical joint.

23. The distracting device according to claim 18, wherein the first and second translational insert each comprises a guide rail, a distal end of each of the first and second translational inserts is provided with a plurality of perforations, and at least a segment of each of the first and second rotatable extensions each comprises rails.

24. The distracting device according to claim 18, wherein the joint is a ball-and-ring-joint.

25. The distracting device according to claim 24, wherein a proximal end of the first rotatable extension is provided with a yoke link, where within the yoke link a ball member is arranged and fixed to one or more hooks of the yoke link by a cross shaft, wherein a bore extends through the yoke link, the ball member, and the cross shaft.

26. The distracting device according to claim 25, wherein the bore enables the positioning of the joint in the flexion-extension axis of the articulating anatomical joint.

27. The distracting device according to claim 24, wherein a proximal end of the second rotatable extension is a ring-shaped member embracing the ball member, with a gap between the ring-shaped member and the ball member.

28. The distracting device according to claim 18, wherein the joint is a cardan joint.

29. The distracting device according to claim 28, wherein the cardan joint comprises a yoke cylinder having a yoke link arranged at a proximal end of the first rotatable extension, a second yoke link arranged at a proximal end of the second rotatable extension, and a center block connected to the yoke link by virtue of a first pin and to the second yoke link by virtue of a second pin, where the first pin and the second pin are mutually perpendicular.

30. The distracting device according to claim 29, wherein a bore extends through the center block and the second pin, and the second yoke link and the second rotatable extension are mutually coupled by a ball bearing.

31. The distracting device according to claim 30, wherein the ball bearing is secured to the proximal end of the second rotatable extension.

* * * * *